(12) United States Patent
Hwu et al.

(10) Patent No.: US 9,402,593 B2
(45) Date of Patent: Aug. 2, 2016

(54) IMAGING OF BIOLOGICAL STRUCTURES BY CHANGING THE POSITION OR DISTANCE OF THE STRUCTURES BETWEEN A SOURCE AND A DETECTOR

(75) Inventors: Yeu-Kuang Hwu, Taipei (TW); Giorgio Margaritondo, Lausanne (CH); Jung Ho Je, Pohang (KR)

(73) Assignee: Academia Sinica, Taipei (TW)

(*) Notice: Subject to any disclaimer, the term of this patent is extended or adjusted under 35 U.S.C. 154(b) by 114 days.

(21) Appl. No.: 13/195,201

(22) Filed: Aug. 1, 2011

(65) Prior Publication Data

US 2011/0288409 A1 Nov. 24, 2011

Related U.S. Application Data (62) Division of application No. 10/435,717, filed on May 8, 2003, now Pat. No. 7,991,454.

(60) Provisional application No. 60/451,854, filed on Mar. 4, 2003.

(51) Int. Cl.
*A61B 6/00* (2006.01)

(52) U.S. Cl.
CPC ............... *A61B 6/482* (2013.01); *A61B 6/481* (2013.01); *A61B 6/484* (2013.01); *A61B 6/504* (2013.01); *A61B 6/508* (2013.01); *A61B 6/4092* (2013.01)

(58) Field of Classification Search
None
See application file for complete search history.

(56) References Cited

U.S. PATENT DOCUMENTS

| | | | |
|---|---|---|---|
| 5,056,524 A | 10/1991 | Oe | 600/431 |
| 5,596,620 A * | 1/1997 | Canistraro | G01B 15/06 378/62 |
| 5,644,646 A | 7/1997 | Du et al. | 382/128 |
| 5,812,629 A * | 9/1998 | Clauser | A61B 6/032 378/37 |
| 5,930,325 A | 7/1999 | Momose | 378/36 |
| 6,018,564 A | 1/2000 | Wilkins | 378/62 |
| 6,311,085 B1 * | 10/2001 | Meaney et al. | 600/420 |
| 6,404,848 B1 * | 6/2002 | Ishisaka | A61B 6/032 378/62 |
| 6,564,085 B2 | 5/2003 | Meaney et al. | 600/415 |
| 6,573,063 B2 | 6/2003 | Hochman | 435/29 |
| 6,671,540 B1 | 12/2003 | Hochman | 600/431 |
| 6,721,590 B2 * | 4/2004 | Ohishi | A61B 6/466 600/425 |
| 6,842,638 B1 * | 1/2005 | Suri | A61B 6/481 382/128 |
| 7,184,516 B2 | 2/2007 | Ohara et al. | 378/62 |
| 7,346,204 B2 | 3/2008 | Ito | 382/132 |
| 2001/0031243 A1 | 10/2001 | Unger | 424/9.51 |

(Continued)

FOREIGN PATENT DOCUMENTS

WO WO0178005 * 10/2001

OTHER PUBLICATIONS

Lee et al. Synchrotron Radiation Imaging of Internal Structures in Live Animals, Yonsei Medical Journal vol. 43, No. 1, pp. 25-30, 2002.*

(Continued)

*Primary Examiner* — Serkan Akar
(74) *Attorney, Agent, or Firm* — Fish & Richardson P.C.

(57) ABSTRACT

Images of blood vessels of a body are obtained by injecting a refraction enhancement contrast agent into the blood vessels to increase a difference in refractive indices of the blood vessels and surrounding material. The blood vessels are irradiated with a penetrating radiation, and an image of the blood vessels is generated based on detected radiation. The image has visible edge enhancement features indicating boundaries of the blood vessels.

15 Claims, 9 Drawing Sheets

(56) References Cited

U.S. PATENT DOCUMENTS

| | | | |
|---|---|---|---|
| 2001/0038707 A1* | 11/2001 | Ohara | 382/132 |
| 2002/0016533 A1 | 2/2002 | Marchitto et al. | 600/310 |
| 2002/0051751 A1* | 5/2002 | Mills | 424/9.361 |
| 2002/0136440 A1* | 9/2002 | Yim et al. | 382/131 |
| 2003/0123611 A1 | 7/2003 | Ohara et al. | 378/98.8 |
| 2004/0167400 A1* | 8/2004 | Kaufman | 600/431 |
| 2005/0080019 A1* | 4/2005 | Wang | 514/23 |

OTHER PUBLICATIONS

Brown et al, Knowledge-based method for segmentation and analysis of lung boundaries in chest X-ray images, Computerized Medical Imaging and Graphics 22 (1998) 463-477.*

Y. Hwu et al. "Coherence-enhanced synchrotron radiology: Refraction versus diffraction mechanisms". Journal of Applied Physics, 86(8):4613-4618, Oct. 15, 1999.

Y. Hwu et al "Use of photoelectron microscopes as X-ray detectors for imaging and other applications". Nuclear Instruments and Methods in Physics Research A437:516-520, 1999.

Y. Hwu et al. "Coherence based contrast enhancement in x-ray radiography with a photoelectron microscope". Applied Physics Letters 75(16):2377-2379, Oct. 18, 1999.

Hee-Joung Kim et al. "Phantom and Aminal Imaging Studies Using PLS Synchrotron X-Rays". IEEE Transactions on Nuclear Science 48(3):837-842, Jun. 2001.

G. Margaritondo et al. "Coherence-based edge diffraction sharpening of x-ray images: A simple model". Journal of Applied Physics 85(7):3406-3408, Apr. 1, 1999.

* cited by examiner

Tracheal wall (labels pointing to features)

IMAGING OF BIOLOGICAL STRUCTURES BY CHANGING THE POSITION OR DISTANCE OF THE STRUCTURES BETWEEN A SOURCE AND A DETECTOR

CROSS REFERENCE TO RELATED APPLICATIONS

This application is a divisional of and claims priority from U.S. application Ser. No. 10/435,717, filed on May 8, 2003, to issue as U.S. Pat. No. 7,991,454, on Aug. 2, 2011, which claims priority to U.S. provisional application 60/451,854, filed on Mar. 4, 2003, the disclosures of which are incorporated here in their entirety.

TECHNICAL FIELD

This invention relates to imaging of biological structures.

BACKGROUND

X-ray imaging is often used to obtain images of internal organs of human or animals. Imaging of blood vessels by x-rays, also called angiography, is routinely performed in clinics to detect artery thrombosis or coronary artery diseases. Clinical angiography requires injecting a contrast agent that has a high x-ray absorption coefficient. The contrast agent includes elements having high atomic numbers, such as iodine. Due to the similarity of the absorption capability between blood, serum, vessels and neighboring tissues, it is difficult to produce recognizable contrast in the radiographs without using contrast agents. Injection of the contrast agents partially replaces the blood in the blood vessel with an x-ray absorbing fluid to create contrast in the x-ray images. The vessels appear darker than surrounding tissues if positive film is used, and brighter if negative film is used.

The materials in the contrast agents that enhance x-ray absorption are generally harmful to the human body, and the injection procedure is often painful and dangerous. Passing absorption contrast agents through body vessels can cause both adverse long and short term side effects to the patient. If not administered safely, the injection process can cause serious injury or even fatality.

SUMMARY

Penetrating radiation can be used to obtain radiographs of internal organs, blood vessels, respiratory system, air passages, digestive systems, ureteral systems, and lymphatic circulating systems of an animal or human body without the use of absorption enhancement contrast materials. Boundaries of the internal organs or blood vessels are determined by detecting a difference in the refractive indices across the boundaries. The contrast of refractive indices is enhanced by injecting a material that increases the difference of refractive indices at the boundaries.

As the penetrating radiation passes through internal body structures that have different refractive indices with respect to the radiation, portions of the radiation are altered by effects such as refraction. The altered radiation and other portions of the radiation in combination produce brighter and/or darker fringes that can be detected by a detector. Because internal body structures often have refractive indices that are different from surrounding tissue or fluid, alteration of radiation caused by differences in refractive indices highlights the edges (or boundaries) of the internal body structures.

The contrast in images obtained by using refraction-based techniques is generally better than the contrast in images obtained by using absorption-based techniques (which depend on the differences in radiation absorption rates of different body parts). Refraction based techniques allow imaging of relatively small internal body structures, such as blood vessels that are less than 10 µm in diameter. In an image generated using differences in refractive indices, the edges of body parts are enhanced. In an image generated using differences in radiation absorption, the entire area of the body part has a different brightness than the surrounding area. Using the same exposure conditions (i.e., exposure time and radiation intensity), the "edge enhancements" created using refraction-based techniques is often more visible than the "area enhancements" created using absorption-based techniques.

Refraction-based imaging techniques are particularly useful when the body part (e.g., soft tissue) to be imaged has a density similar to tissue or fluid, and is composed of elements with similar atomic numbers as the surrounding tissue or fluid. For such a body part, the difference in the absorption rates of the body part and its surrounding material (e.g., tissue or fluid) is small, and as a consequence, there may not be sufficient contrast for the body part to become visible in the image if absorption-based imaging techniques are used. Also, for small body parts (e.g., blood vessels less than 10 µm in diameter), even if their radiation absorption rate is different compared to surrounding tissue or fluid, due to their small size, the difference in the amount of absorption may not be visible in the image when absorption-based imaging techniques are used.

In one aspect, the invention features a method that includes injecting a refraction contrast agent into a blood vessel to increase a difference in refractive indices of material inside the blood vessel and material outside of the blood vessel, irradiating the blood vessel with a penetrating radiation, and generating an image of a portion of the blood vessel based on detected radiation.

Implementations of the invention may include one or more of the following features.

The image is generated without using a material that enhances absorption of the radiation inside the blood vessel.

The image has an edge enhancement feature indicating a boundary of the portion of the blood vessel.

The edge enhancement feature is caused by refraction or diffraction, or both, of the radiation at the boundary.

The edge enhancement feature includes a line positioned along the boundary, the line having an average diameter less than half the average diameter of the blood vessel.

The refraction contrast agent increases the refractive index of the material inside the blood vessel.

The refraction enhancement contrast agent includes artificial serum, alcohol, oil, collagen based fluid, polymer based fluid, gases having an atomic number less than 40, or any combinations of the above materials.

In another aspect, the invention features a method that includes irradiating a blood vessel with a penetrating radiation, generating an image of a portion of the blood vessel based on detected radiation. The radiation is selected to have a wavelength and effective source size such that the image has an edge enhancement feature that indicates a boundary of the blood vessel. The edge enhancement feature is caused by refraction of the penetrating radiation near the boundary.

Implementations of the invention may include one or more of the following features.

The edge enhancement feature includes a line that has an average diameter less than half the average diameter of the blood vessel.

The radiation is generated from a source, which when viewed from the blood vessels, extends an angle that is less than 1 mrad.

The radiation comprise components having wavelengths smaller than 10 angstroms.

The method also includes increasing a contrast between the edge enhancement feature and areas near the edge enhancement feature by adjusting a distance between the blood vessel and a detector used to detect the radiation.

The method also includes generating a second image after the image is obtained, and comparing the image and the second image to detect a movement of the blood vessel.

The method also includes generating a video showing movements of the blood vessel by generating a sequence of images, each image including edge enhancement features caused by refraction of the radiation near the boundary of the blood vessel.

The method also includes detecting a presence of a tumor having outer diameters less than 10 mm by detecting a concentration of blood vessels In another aspect, the invention features a method that includes injecting a refraction contrast agent into an internal portion of a body to increase a difference in refractive indices of material inside the internal portion and material outside of the internal portion, irradiating the internal portion with a penetrating radiation, and generating an image of the internal portion based on detected radiation.

Implementations of the invention may include one or more of the following features.

The internal portion includes a portion of a heart, a lung, a liver, a kidney, tissue forming an air passage, a digestive organ, an organ of a ureteral system, or an organ of a lymphatic circulating system of a human.

The internal portion includes a portion of a heart, a lung, a liver, a kidney, tissue forming an air passage, a digestive organ, an organ of a ureteral system, or an organ of a lymphatic circulating system of an animal.

In another aspect, the invention features a method that includes irradiating an internal portion of a body with a penetrating radiation, and generating an image of the internal portion based on detected radiation, the radiation having a wavelength and effective source size selected such that the image has edge enhancement features that indicate edges of the internal portion, the edge enhancement features caused by refraction of the penetrating radiation near the edges.

In another aspect, the invention features a method that includes irradiating a blood vessel with a penetrating radiation, and generating a first image and a second image of the blood vessel based on the radiation. The first image has edge enhancement features that indicate edges of the blood vessel. The second image has reduced edge enhancement features. A third image is generated based on the first and second images, the third image having edge enhancement features with a contrast greater than the edge enhancement features of the first image.

Implementations of the invention may include one or more of the following features.

Generating the third image includes subtracting the second image from the first image.

The edge enhancement features include a dark line adjacent to an edge of the blood vessel.

In another aspect, the invention features a method that includes inserting objects into a blood vessel of a body, irradiating the blood vessel with a penetrating radiation, and generating an image of the objects based on detected radiation, the image including edge enhancement features that indicate boundaries of the objects.

Implementations of the invention may include one or more of the following features.

The objects have refractive indices that are different from a wall of the blood vessel.

The objects have refractive indices that are different from material outside of the blood vessel.

The edge enhancement features are caused by refraction of the radiation at edges of the objects.

The method also includes deriving an image of the blood vessels from the image of the objects.

The objects include small gas bubbles comprising gas of atomic number less than 40 or plastic beads, or a mixture of the above materials.

The plastic beads have diameters less than 1 mm.

The method also includes generating successive images of the objects at different period of time to detect a movement of the objects through the blood vessels.

In another aspect, the invention features an apparatus for angiography that includes an imaging device to generate images of blood vessels based on penetrating radiation irradiated on the blood vessels, and a data processor configured to generate a third image based on differences in a first image and a second image obtained by the imaging device at two different positions relative to the blood vessels, the third image having edge enhancement features indicating edges of the blood vessels, the edge enhancement features caused in part by refraction of the penetrating radiation at edges of the blood vessels.

Implementations of the invention may include one or more of the following features.

The apparatus also includes an injector for injecting a refraction enhancement contrast agent into the blood vessels.

In another aspect, the invention features an apparatus for angiography that includes a support for supporting a body having blood vessels, a light source to generate a penetrating radiation that is irradiated on the blood vessels, and an imaging device to generate images of the blood vessel based on detected radiation, the light source having a wavelength and an effective source size selected so that the imaging device can generate images of the blood vessels, the images having edge enhancement features indicating edges of the blood vessels, the edge enhancement features caused by refraction of the penetrating radiation at the edges of the blood vessels.

Implementations of the invention may include one or more of the following features.

The apparatus also includes an aperture to adjust the effective source size.

In another aspect, the invention features an apparatus that includes a support for supporting a body having blood vessels, and means for generating an image of the blood vessels based on penetrating radiation that is irradiated on the blood vessels, the image having edge enhancement features indicating boundaries of the blood vessels, the edge enhancement features caused by refraction of the radiation at edges of the blood vessels or by refraction of the radiation at edges of objects in the blood vessels.

Implementations of the invention may include one or more of the following features.

The apparatus also includes means for injecting a refraction contrast agent into the blood vessels to change the refractive index of material inside the blood vessel.

The apparatus also includes means for detecting movements of the blood vessels based on the edge enhancement features.

The apparatus also includes means for injecting objects into the blood vessels, the objects having refractive indices that are different from walls of the blood vessels or different from material outside of the blood vessels.

The apparatus also includes means for processing two images of the blood vessels to enhance features that indicate boundaries of the blood vessels.

Other features and advantages of the invention will be apparent from the description and drawings, and from the claims.

DESCRIPTION OF DRAWINGS

FIGS. 3A-5 show images of live blood vessels.

Like reference symbols in the various drawings indicate like elements.

DETAILED DESCRIPTION

Figure 1:
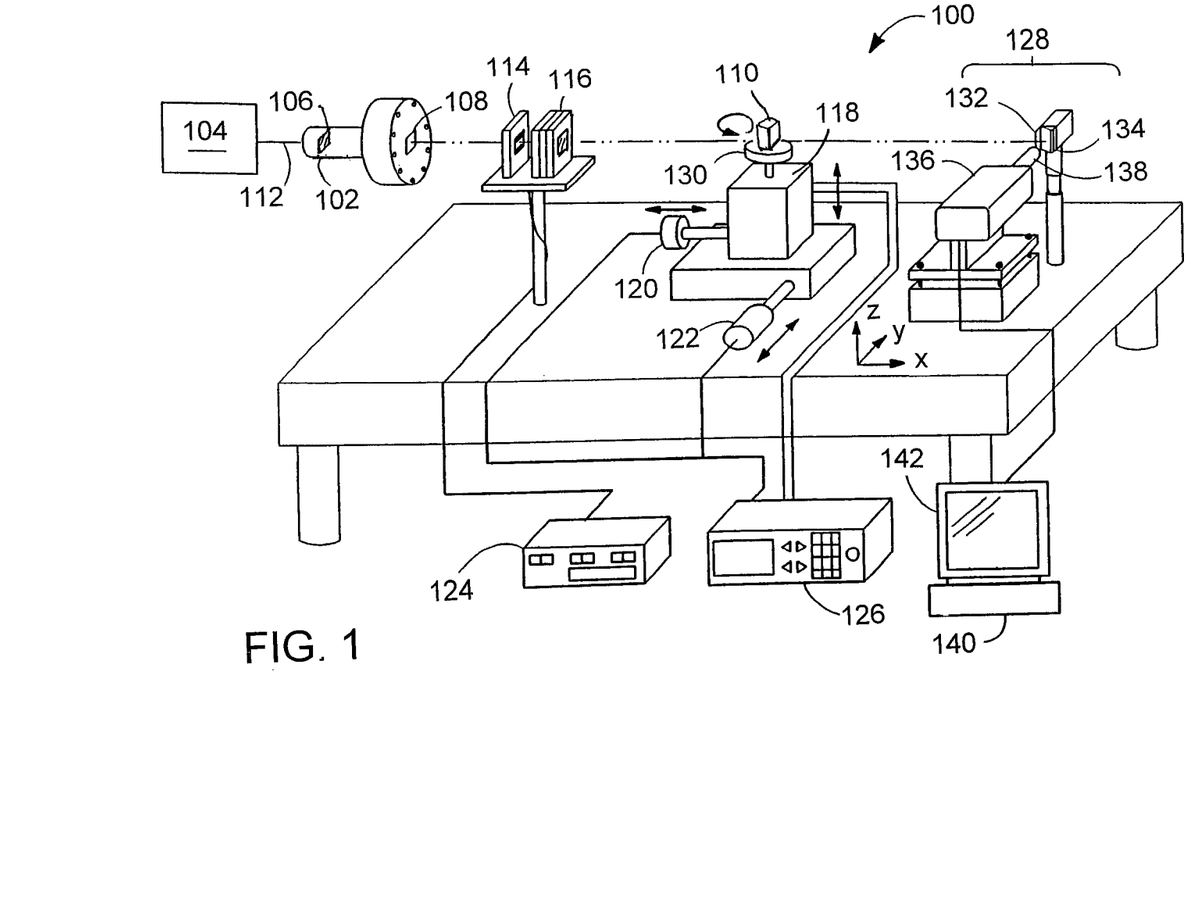
FIG. 1 is an x-ray imaging system.

Referring to FIG. 1, a penetrating radiation imaging system 100 includes a radiation guide 102 that receives a beam 112 of penetrating radiation (e.g., x-ray) from a radiation source 104 (e.g., a synchrotron). Source 104 produces penetrating radiation having wavelengths that are shorter than 1 nm. The penetrating radiation is irradiated on a measurement object 110 and detected by a detector unit 128. Object 110 may be a live animal.

The term "penetrating radiation" refers to radiation having sufficiently high energy that can pass through the object being imaged. Examples of penetrating radiation are x-rays and gamma rays. Beam 112 may have a wavelength less than 0.03 nm when system 100 is used to image internal structures of humans, and may have a wavelength of about 0.08 nm when system 100 is used to image small animals.

The radiation source 104 is designed to have a small effective size (i.e., the size of the radiation source as seen from object 110) so that effects due to refraction are not washed out by superposition of patterns generated from different portions of the radiation source. The effective size of radiation source 104 can be reduced by using a smaller radiation source and/or by placing the radiation source 104 at a longer distance away from object 110. Reducing the effective size of the radiation source 104 reduces the intensity of beam 112 on object 110. The effective size of the radiation source 104 is selected so that beam 112 has sufficient intensity to create recognizable images with a sufficient level of detail.

When beam 112 is directed towards object 110, portions of beam 112 refract as they pass through object 110 because different parts of object 110 have different refractive indices. The refraction results in edge enhancement features in the images that indicate the boundaries of the different parts. Beam 112, after passing through object 110, is detected by detector unit 128. Detector unit 128 produces an image that shows boundaries of the object's internal structures.

In one example, the effective size (i.e., cross sectional area as seen from object 110) of the radiation source 104 is selected to be sufficiently small such that refraction enhancement features are not "washed out," as would happen if a radiation source having a larger size were used. When a radiation source with larger effective size is used, radiation from different portions of the source interfere with one another, hence washing out the refraction enhancement features. As an example, to view a blood vessel less than 1 mm in diameter, a source extending less than 1 mrad (~0.06 degrees) (as seen from object 110) can be used, Beam 112 does not have to be monochromatic, i.e., having a single wavelength or a wavelength within a very narrow range. Thus, white light (i.e., radiation having a continuous spectrum of wavelengths) from a synchrotron may be used in system 100.

System 100 includes a slit module 114 and a controllable attenuator 116 that are positioned between light guide 102 and object 110. Slit module 114 adjusts the cross section dimension of beam 112, and controllable attenuator 116 controls the intensity of the beam 112. Controllable attenuator 116 is controlled by attenuator controller 124. A fixed attenuator 106 is placed in light guide 102 to reduce the intensity of the penetrating radiation to a safe level.

System 100 includes a rotatable stage 130 connected to a translatable stage 118. Rotatable stage 130 supports object 110 and can be rotated relative to translatable stage 118. Stepper motors 120 and 122 adjust the position of stage 118 in the X- and Y-direction, respectively, relative to detector unit 128. A third stepper motor (not shown) inside stage 118 adjusts the position of stage 130 in the Z-direction relative to detector unit 128. The stepper motors are controlled by a motor controller 126.

Stages 118 and 130 are adapted to support the object to be imaged. Where object 110 represents a human patient, the stages are replaced by larger supports designed to allow the human patient to lie or sit comfortably while radiographs are taken.

The detector unit 128 includes a scintillator 132 and a CCD camera 136. Scintillator 132 converts the penetrating radiation of beam 112 into light having a wavelength that is detected by CCD camera 136. In this embodiment, scintillator 132 is made of cadmium tungstate ($CdWO_4$). A magnifying lens 138 is used to enlarge the image of the irradiated portion of object 110. Signals generated by camera 136 are sent to an image acquisition system 140, which includes a display 142 for displaying the images obtained by CCD camera 136. Image acquisition system 140 includes a storage device (not shown), such as a hard disk drive, for storing the images.

Figure 2:
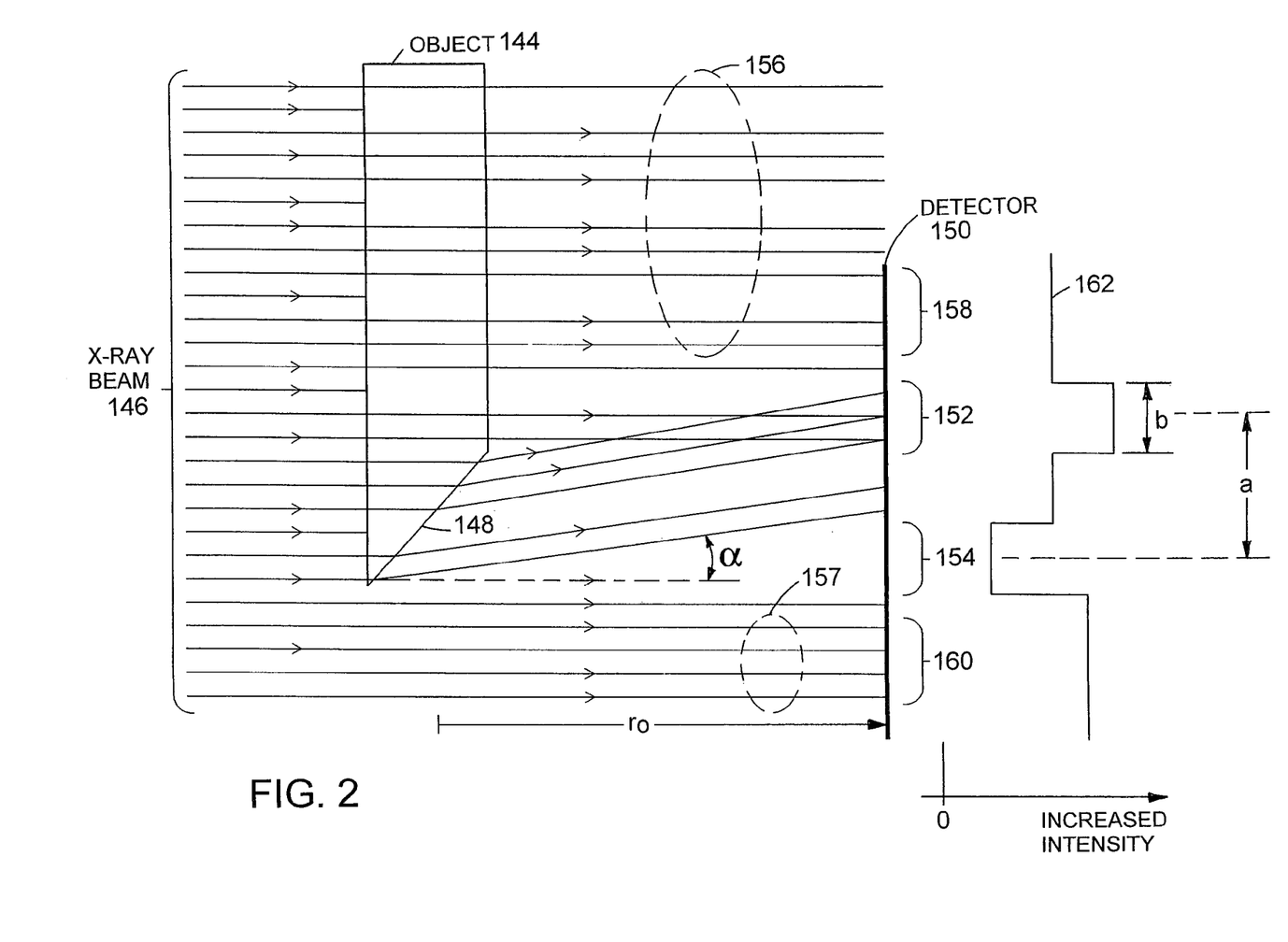
FIG. 2 is a diagram showing x-ray refraction.

With reference to FIG. 2, the principles of edge enhancement based on refraction are described. An object 144 (e.g., a body part or an object inserted into an internal portion of a body) having a tapered edge 148 is illuminated by an x-ray beam 146. Object 144 is surrounded by a medium that has a refractive index different from the refractive index of object 144. The x-ray beam 146 for illuminating object 144 and surrounding medium is detected by a detector 150. The beam intensity in an area 156 is lower (compared to the bean intensity in an area 157) due to absorption of x-rays by object 144.

Because the refractive indices of object 144 and the surrounding medium are different, x-rays passing through the tapered edge 148 will refract and change propagation direction. The propagation direction of the refracted x-rays deviate from the original propagation direction by an angle α that depends on the edge slope and on the real part of the refractive index of object 144. The angular displacement a causes a brighter fringe 152 and a darker fringe 154 to appear at the detector 150. Edge enhancement features that include the brighter fringe 152 and darker fringe 154 indicate the edge or boundary of object 144. The term "brighter" means that the intensity of the radiation is higher and does not mean that it appears brighter to a human eye since the radiation may be invisible to the eye.

The intensity of x-rays detected by detector 150 has a profile 162 with enhanced features at the position of edge 148. The intensity of radiation at a region 158 is lower than the intensity of radiation at a region 160 due to absorption of x-rays by object 144. The darker fringe 154 has an intensity lower than that of region 158 because the rays were refracted away from region 154. The brighter fringe 152 has an intensity higher than region 160. The higher intensity is caused by a summation of refracted rays and rays that are not refracted.

Edge enhancements based on refraction result in the brighter fringe 152 and the darker fringe 154. This enhances visibility of tapered edge 148, making it easier determine the boundary of object 144. When applied to angiography, edge enhancements based on refraction allow a doctor to see the boundaries of blood vessels of a patient more clearly.

If the intensities in areas 158 and 160 are high, the contrast between the brighter fringe 152 and areas 158, 160 is lower, while the contrast between the darker fringe 154 and areas 158 and 160 is higher. In this situation, the edge enhancement features appear as a darker line in a lighter background. Conversely, if the intensities in areas 158 and 160 are low, the contrast between the brighter fringe 152 and areas 158, 160 is higher, while the contrast between the darker fringe 154 and areas 158, 160 is lower. In this situation, the edge enhancement features appear as a brighter line in a darker background.

Edge enhancements based on refraction are most significant when the distance $r_0$ between object 144 and detector 150 falls within a certain range. The average distance a between the darker and brighter fringes appearing on the detector is determined by the width of the tapered edge in a direction perpendicular to the propagation direction of the x-rays. The fringes have an average width b that increases roughly proportional to $r_0$, and can be written as $b \leq r_0 \cdot \alpha$. The fringe width b also depends the shape of the edge 148 (which affects $\alpha$) and the real part of the refractive index of object 144. When fringe width b becomes larger than a, it becomes more difficult to distinguish between the darker fringe 154 and the brighter fringe 152 from each other and from the other regions. Thus, the enhancements due to refraction become less visible when $r_0$ increases above a threshold distance, which depends on the geometry of the object being measured. The distance $r_0$ should be large enough so that the distance between the darker and brighter fringes is sufficiently far apart to be resolved by detector 150.

Referring again to FIG. 1, to obtain images of internal structures of object 110, stage 118 is initially positioned closer to detector unit 128, then moved in a direction away from detector unit 128. If object 110 has a complex internal structure, there will be tapered edges with different widths and edge slopes, causing rays to refract at different angles. The edge enhancements based on refraction will be more prominent for different internal structures when stage 118 is positioned at different locations.

An adjustable aperture 108 is used to reduce the effective size of radiation source 104 as viewed by object 110 so that the effective size is smaller than the deviation of beam 112 caused by refraction. The effective size of the radiation source can also be reduced by increasing the distance between radiation source 104 and object 110. The distance (e.g., $r_0$ in FIG. 2) between detector unit 128 and object 110 is adjusted to increase the visibility of the refraction based edge-enhancement effects with respect to detector unit 128. Adjustment of the distance between detector unit 128 and object 110 depends on the feature size that a user wishes to visualize. For example, if one intends to visualize a blood vessel of 100 µm in size, the edge enhancement features (the dark and/or bright fringes) would be designed to be smaller than about half the blood vessel size (50 µm).

FIGS. 3A-3E show images of blood vessels of a 12-week old male rat (Sprague Dawley, body weight about 200 gm). The rat was generally anesthetized and monitored according to standard animal care procedures. The images were obtained using unmonochromatized synchrotron x-rays (white beam). The x-rays came from a 5C1 beam line of the Pohang Light Source in Korea. The rat was positioned upright with an animal holder on top of stage 130. The images in FIGS. 3A-3E have the same magnification. The scale bar 190 represents 200 µm. The exposure time of each image in FIGS. 3A-3E was 15 milliseconds.

Figure 3A:
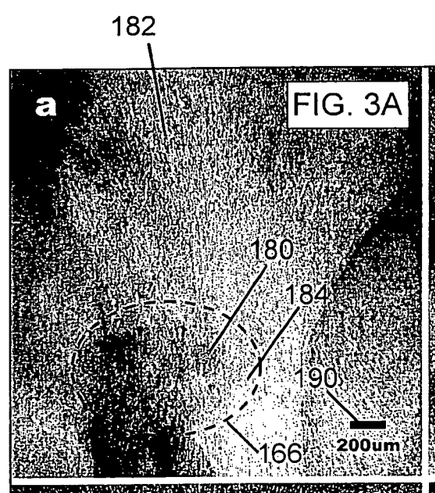
Figure 3B:
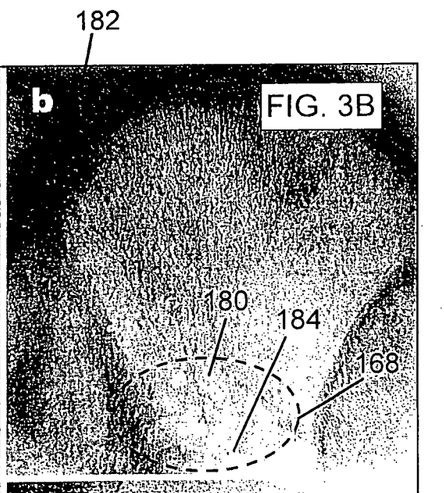

FIGS. 3A and 3B show draining vessels (e.g., 180) of an eyeball 182 of the rat. Intertwined blood vessels are visible and are representative of choroidal blood vessel networks. In FIG. 3A, before the image was taken, the blood vessels were injected with a small amount of diluted iodine contrast dye (Imagopaque®, 300 mg I/ml, 0.3 ml, diluted by one half with normal saline in a 1.0 ml syringe). The contrast dye was injected through the proximal common carotid artery at the anterior neck with a fine polyethylene tube (having an outside diameter of 0.8 mm). The tube was inserted about 5 mm towards the head before the carotid bifurcation. The contrast agent was used to show that the observed features are indeed live blood vessels.

In FIG. 3B, the image was taken several minutes after the contrast dye has passed through the vessel. The image shows edge enhancement features (darker lines) that indicate the boundaries of the small vessels (see encircled region 168). The edge enhancement features are the result of refraction at the edges of the blood vessels.

Some visible blood vessels in FIG. 3A and FIG. 3B have outer diameters less than 200 µm.

A comparison of a region 166 in FIG. 3A and region 168 in FIG. 3B shows that the vessel walls (e.g., 184) are more visible without the iodine contrast dye. There are two reasons for this. First, the iodine contrast dye absorbs a portion of the refracted x-rays, so fewer x-rays are detected to produce the brighter and darker fringes. Second, the iodine contrast dye reduces the difference between the refractive indices of materials inside and outside of the blood vessels.

Figure 3C:
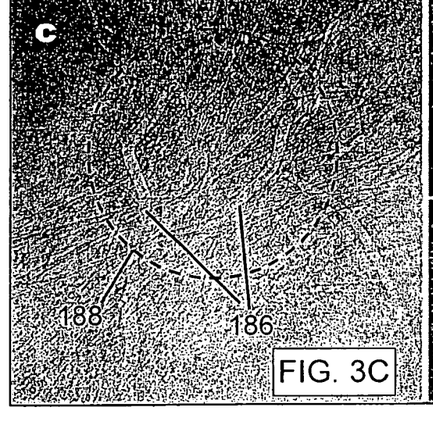
Figure 3D:
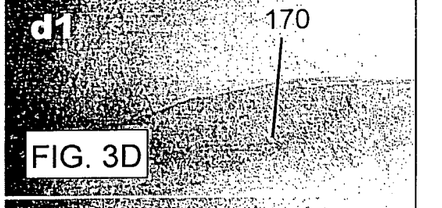
Figure 3E:
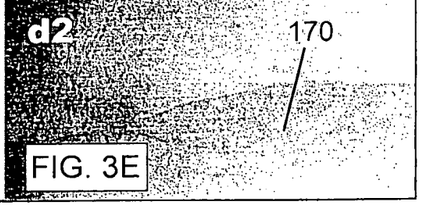

FIGS. 3C-3E show tree-like auricle blood vessels (e.g., 186) having widths of 8 to 100 µm. FIG. 3C shows blood vessels from a different part of the same mouse as FIGS. 3A and 3B. The blood vessels have tree-like features (e.g., 188, enclosed in dash lines) that were previously difficult to image in live animals. The image in FIG. 3C was obtained after the passage of the iodine contrast dye.

FIGS. 3D and 3E show a comparison of the same vessel during and after the passage of the iodine contrast dye. In FIG. 3D, a blood vessel 170 appears slightly darker than surrounding tissue. Blood vessel 170 appears darker near the central region (because the x-rays have to pass through a thicker portion of the contrast dye) and less dark toward the edges. There is no clear boundary between blood vessel 170 and surrounding tissue. In FIG. 3E, for the same blood vessel 170, there are edge enhancement features indicating the boundaries of the blood vessel. The edge enhancement features appear as dark lines (one dark line along each side of the blood vessel) positioned along the blood vessel walls, showing the boundary between the blood vessels and surrounding tissue.

Comparing FIGS. 3D and 3E shows that absorption-based enhancement effects cause the entire blood vessel to be enhanced, but with a lower contrast. Refraction-based enhancement effects cause only the boundaries to be enhanced, and with a higher contrast.

Figure 4:
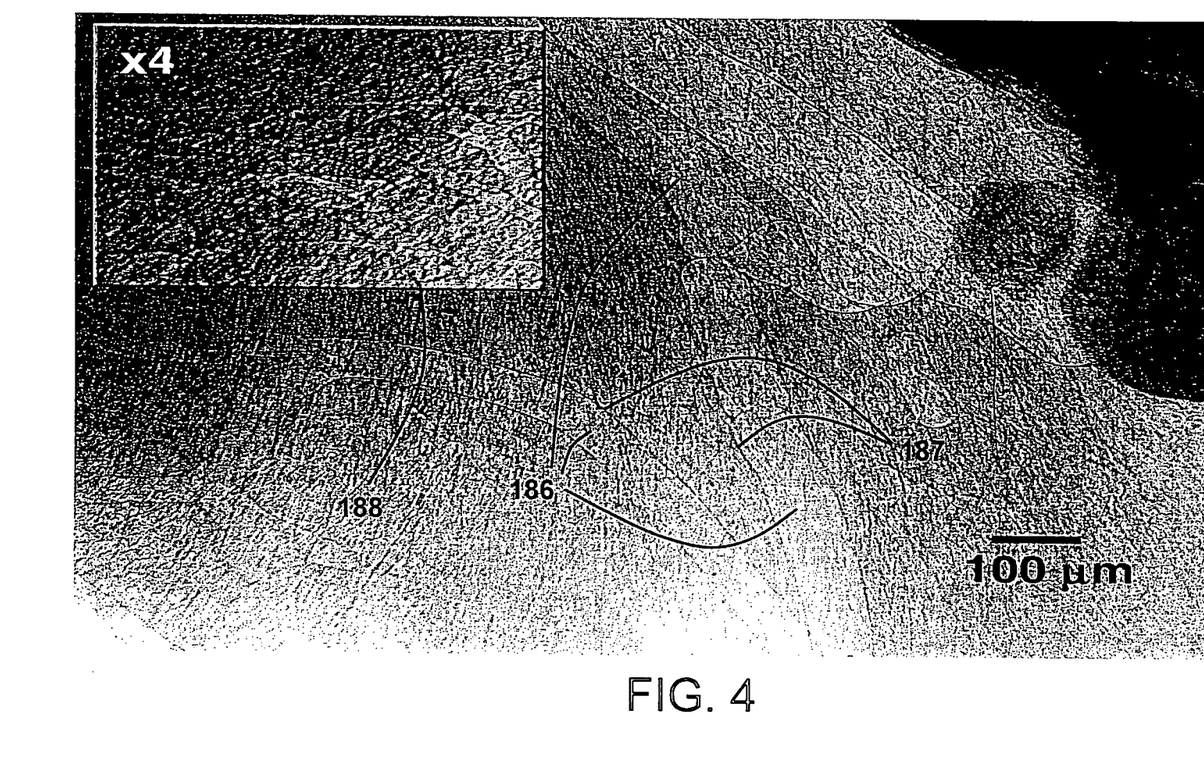

FIG. 4 shows images of blood vessels of a female mouse (ICR, 24.7 gm, Daehan Biolink Co., Korea). The images in FIG. 4 were obtained without injection of a contrast dye to enhance absorption of x-rays. The larger image shows blood vessels (e.g., 186) in an area near the ankle. It has good resolution and contrast. The scale bar represents 100 µm. An inset 188 shows an enlarged image taken from a different region of the leg of the same mouse. The outer diameters of some of the blood vessels in inset 188 are smaller than 20 µm. For each image, the exposure time was about 30 milliseconds.

In the images of FIG. 4, blood vessels 186 have edge enhancement features that indicate the boundaries of the blood vessels. In this example, the edge enhancement features are thin lines 187 positioned along the boundaries of the blood vessels 186.

By using edge enhancements based on refraction, images of blood vessels can be obtained in a short amount of time. Successive images of the blood vessels can be taken to show movements of the vessels. A video of the movements of the blood vessels may be generated. The images can be stored (e.g., by image acquisition system 140) for later use.

Figure 5:
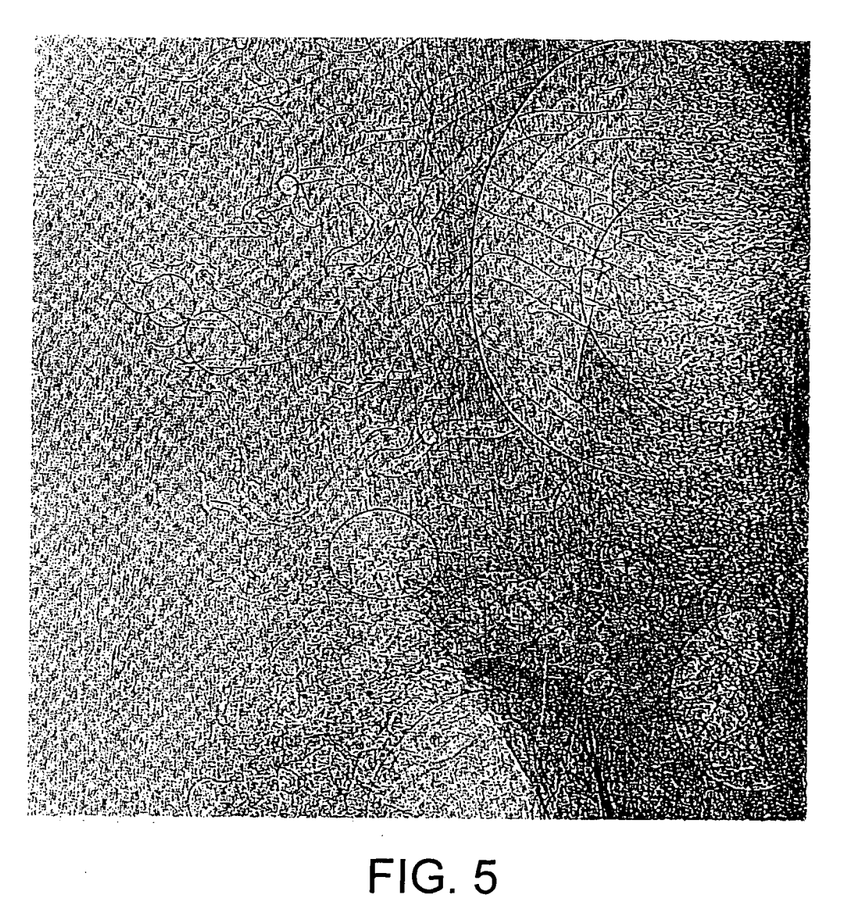

FIG. 5 shows an image of organs and blood vessels of a mouse. The image was taken from the lower body near the pelvis of a male mouse (ICR, 30.2 gm, Daehan Biolink Co., Korea). No contrast agent was used when this image was taken. The width of the entire image corresponds to about 1 cm. The image shows that blood vessels having an outer diameter less than 10 µm can be observed.

The images of FIGS. 3A-5 demonstrate that high-resolution micro-angiography can be implemented without the complications caused by injection of absorption enhancement contrast dyes. Using edge enhancements based on differences in refractive indices at edges of blood vessels, images of blood vessels less than 10 µm may be obtained. The ability to image small vessels allows a doctor to detect changes in morphological parameters (i.e., the length and diameter of blood vessels or the number of bifurcation points) to detect vascular diseases.

For example, the luminal narrowing of the heart coronary arteries and the brain small arteries cause heart and cerebral stroke, respectively, due to arteriosclerosis. In the past, it was difficult to detect such features because injecting absorption enhancement contrast dyes into these arteries could cause injury to the patient. Using angiography techniques that do not use absorption enhancement contrast agents will improve diagnosis of such ailments.

Figure 6:
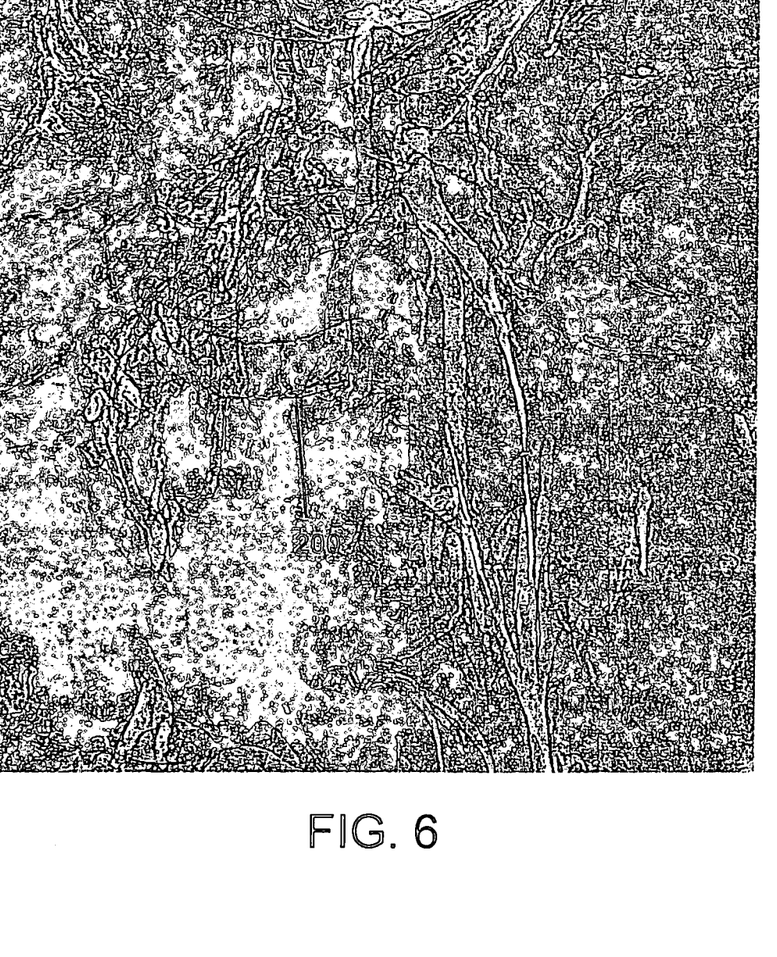
FIG. 6 shows blood vessels of a liver in a patient who had liver cancer.

Angiography techniques that do not use absorption enhancement contrast agents can also be used to detect tumors by detecting micro-vessels in the tumors. Tumor tissues require nutrition and oxygen for growth and metastasis. Tumor tissues often form new, thin blood vessels (neovascularization) to supply nutrition and oxygen. These new blood vessels may have an outer diameter less than 100 µm. By detecting a clustering of micro-vessels, the probability of detecting tumor at its early stages is increased. An example is shown in FIG. 6, which shows an agglomeration of blood vessels 200 in a sliced tissue from the liver of a liver cancer patient Angiography techniques that do not use absorption enhancement contrast agents may be applied in the study of angiogenesis (vessel formation) and oncogenesis (tumor development). It can also be used in the early detection of tumors and vascular problems, and detection of abnormal changes in the natural movements of vital organs.

An advantage of angiography techniques that do not use absorption enhancement contrast dyes is that when taking images of a small portion of the body, it is not necessary to inject contrast dyes that circulate through a large portion of the body, causing side effects to the larger portion of the body.

The images of blood vessels can be further enhanced by injecting refraction contrast agents that can dissolve in blood serum and increase the difference of refractive indices of the blood serum and the blood vessel walls. Contrast agents that increase the difference of refractive indices between materials inside and outside of the blood vessel walls can also be used. Such contrast agents that affect refractive indices are different from absorption-enhancement contrast agents.

In the examples below, refraction enhancement contrast agents are used to increase the refractive index of the material inside the blood vessels or internal organs. Refraction reduction contrast agents can also be used to decrease the refractive index of the material inside the blood vessels (or internal organs) so as to increase the difference in refractive indices between the materials inside and outside the blood vessels (or internal organs).

Refraction enhancement contrast agents can be more biologically compatible and safer to the body because these contrast agents do not use high atomic number elements (which is commonly used in absorption contrast agents). Using such refraction enhancement contrast agents is usually more comfortable to the patient. Materials having properties similar to blood or serum can have very different refractive index values from blood or serum. Examples of materials that can be used to enhance refraction include collagen, polymer, artificial serum, alcohol, oil, emulsion, polymer based fluid, or gases having lower atomic numbers.

Small particles that cannot be directly detected by the detector unit (e.g., 128) but whose presence modifies the overall refractive index of the fluid in the blood vessels can be used to enhance contrast at the boundaries between the fluid that contains those particles and the fluid or tissue that do not contain those particles.

Small objects (such as micro bubbles, capsules, or plastic beads), that have refractive indices different from the refractive index of blood can also be injected into blood vessels. In one example, the objects have dimensions less than 1 µm. Edge enhancements based on refraction can enhance the boundaries of those objects, and images of blood vessels can be derived from images of the small objects.

In the past, to obtain x-ray images of lungs, patients have to inhale absorption enhancement contrast gases, such as xenon, to increase the quality of the images. There can be adverse side effects in inhaling xenon. Using edge enhancements based on refraction, the patient no longer has to inhale gases containing high atomic number elements. Edge enhancements based on refraction can be used to obtain images of bronchia walls, trachea walls, lung, and alveolar.

Figure 7A:
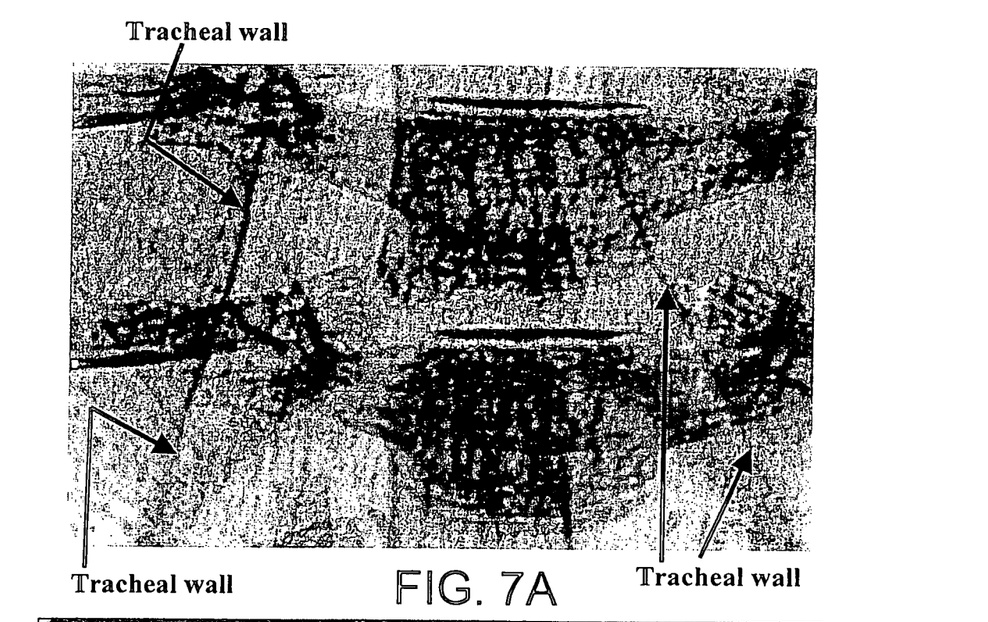
FIG. 7A shows the trachea of a mouse.

FIG. 7A shows an example of a portion of the lung of the same mouse as shown in FIG. 5. The photo shows a portion of the trachea, with markings showing the tracheal walls.

Figure 7B:
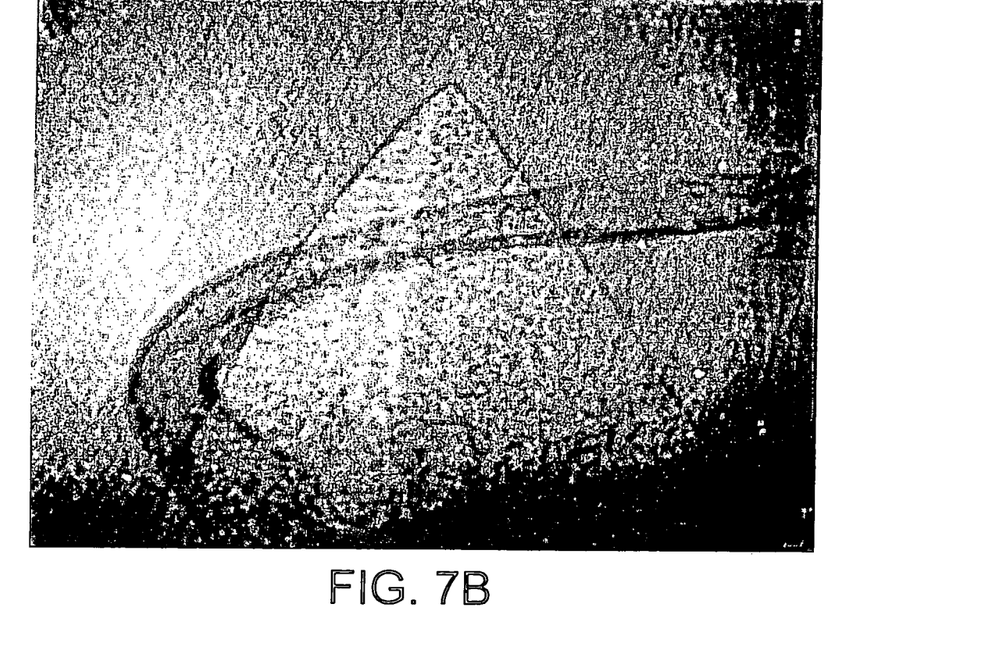
FIG. 7B shows lung cells of a mouse.

FIG. 7B shows a portion of the lung, the rough texture indicating the radiation being refracted by small lung cells. If the radiation wavelength and effective source size were selected so that effects due to refraction wash out, the texture of the lung would be smooth.

Figure 8:
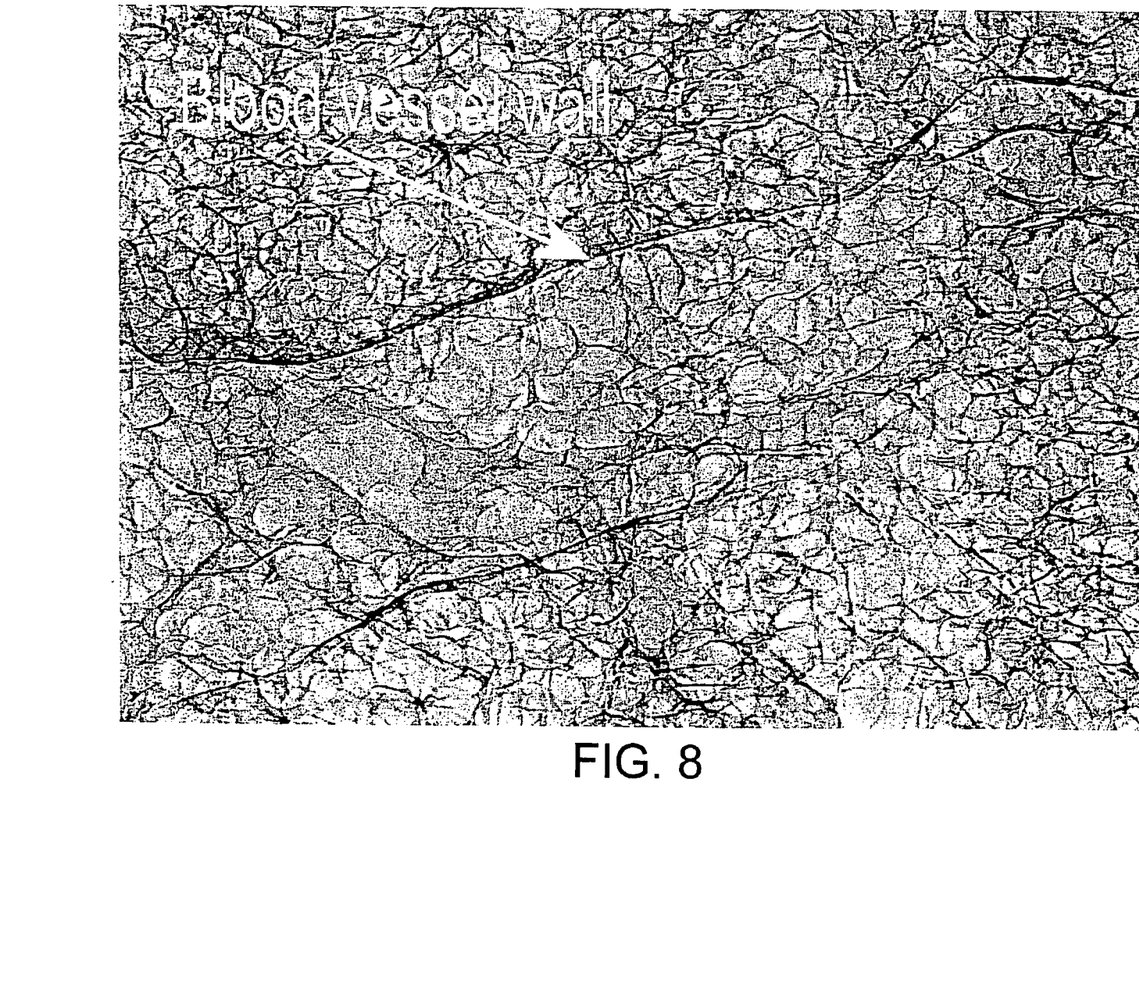
FIG. 8 shows lung cells of a pig.

FIG. 8 shows an image of lung cells and blood vessels that were taken from a slide containing tissue obtained from an inflated pig lung. The edge enhancement features (seen in the image as darker lines, e.g., 202, and brighter lines, e.g., 204) indicate boundaries of the cells or blood vessels.

An advantage of using edge enhancement based on refraction is that images of smaller blood vessels can be obtained. When absorption enhancement contrast agents are used, to obtain sufficient contrast, the concentration of the contrast agents cannot be too low. When the blood vessels are very thin, such as those having a diameter less than 200 μm and shown in FIG. 3A, the contrast enhancing effect of the absorption enhancement contrast agent is much reduced. Thus, using techniques that use absorption enhancement contrast agents, it is difficult to image blood vessels having a diameter less than 100 μm in a mouse body that is 30 mm thick. By comparison, enhancement of edges or boundaries of materials having different refractive indices allows detection of blood vessels having a diameter less than 10 μm. This is true even when those blood vessels are enclosed by a thick body part, as demonstrated in FIGS. 3A-8.

Figure 9A:
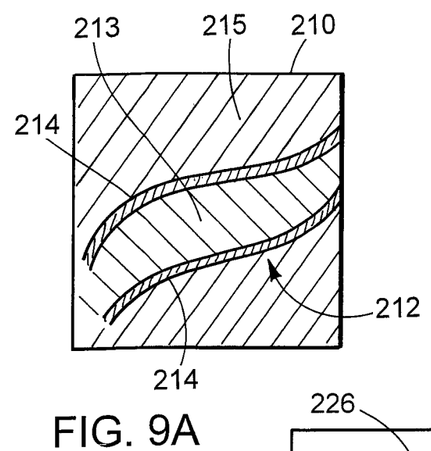
FIGS. 9A-9C are diagrams representing images of a blood vessel with edge enhancement features.
Figure 9B:
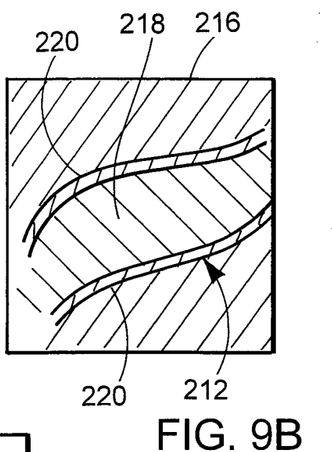
Figure 9C:
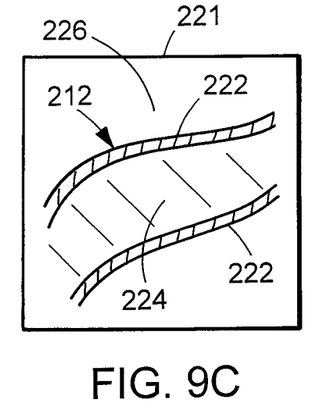

Referring to FIGS. 9A-9C, the edge enhancement features may be further enhanced by detecting differences in two images, one with edge enhancement features, the other with reduced edge enhancement features. To illustrate this technique, the setup in FIG. 1 is used, and an animal having blood vessels is used as object 110. As discussed previously, edge enhancements based on refraction are most significant when the distance between object 110 and detector unit 128 falls within a certain range. Initially, object 110 is placed at a first distance from detector unit 128 such that the first distance falls within the certain range. Detector unit 128 generates a first image 210 having a blood vessel 212. In image 210, blood vessel 212 has edge enhancement features 214 that are darker than a center region 213 and darker than areas 215 outside of the blood vessel. The first image 210 is sent to the image acquisition system 140.

Object 110 is then positioned at a second distance from detector unit 128 such that the first distance falls outside of the certain range. Detector unit 128 generates a second image 216 of blood vessel 212. In the second image 216, blood vessel 212 has reduced edge enhancement features 220 (i.e., the contrast between the edge enhancement features 220 and adjacent areas is reduced). The second image is sent to image acquisition system 140.

Image acquisition system 140 has a data processor that generates a third image 221 by subtracting the second image 216 from the first image 210. The third image 218 shows edge enhancement features 222 that has a contrast (compared with a region 224 inside the blood vessel and a region 226 outside the blood vessel) greater than the contrast of edge enhancement features 214 in image 210. Comparing images 210 and 216, the difference in brightness (or darkness) of the edge enhancement features is greater than the difference in brightness (or darkness) at regions inside and outside the blood vessel. This causes the edge enhancement features 222 to be more prominent in image 221.

Although some examples have been discussed above, other implementation and applications are also within the scope of the following claims. For example, beam 112 can have different wavelengths, and can be generated from different radiation sources. Examples of penetrating radiation include micro-focus x-rays generated from bombardment of a metal target, x-rays generated by laser plasma, neutron beams, and gamma rays. Instead of X-ray, a beam of neutrons can also be used as the penetrating radiation. Detector unit 128 can be any device sensitive to the penetrating radiation and with sufficient resolution to show the refraction-enhancement features. Detector unit 128 may include film that is sensitive to the penetrating radiation. In the description above, refraction enhancement techniques were described. Using the apparatus of FIG. 1, diffraction enhancement can also be used if beam 112 has sufficient longitudinal coherence. By adjusting the distance between object 110 and detector unit 128, it is possible to detect edge enhancement effects due to diffraction at edges of internal structures of object 110.

What is claimed is:

1. A method comprising:
    inserting a contrast agent comprising objects into a blood vessel of a body, the objects having refractive indices different from the refractive index of blood with respect to a penetrating radiation having a wavelength of 1 nm or less, the difference in refractive indices being sufficient to provide visible edge enhancement features in images of the objects in blood vessels that contain the objects in which the images are obtained using the penetrating radiation, the edge enhancement features being caused by refraction of the penetrating radiation at boundaries of the objects;
    placing the body on a stage wherein the stage is positioned between a penetrating radiation source and a detector;
    irradiating the body including the blood vessel with the penetrating radiation having the wavelength of 1 nm or less, causing refraction of the penetrating radiation at the boundaries of the objects, generating edge enhancement features that include at least one of brighter or darker fringes;
    adjusting a position of the body via the stage relative to the detector by moving the body from a first distance relative to the detector to a second distance relative to the detector, in which when the body is at the first distance relative to the detector, the edge enhancement features are less visible, and when the body is at the second distance relative to the detector, the edge enhancement features are more visible, to cause the at least one of brighter or darker fringes produced by the refraction of the penetrating radiation occurring at the boundaries of the objects that are inserted into the blood vessel to be detected by the detector; and
    generating an image of the objects with the blood vessels based on the detected radiation, the image including edge enhancement features that indicate the boundaries of the objects, in which the edge enhancement features are generated based on the refraction of the penetrating radiation at the boundaries of the objects.

2. The method of claim 1 in which the objects have refractive indices that are different from a wall of the blood vessel.

3. The method of claim 1 in which the objects have refractive indices that are different from material outside of the blood vessel.

4. The method of claim 1, further comprising deriving an image of the blood vessels from the image of the objects.

5. The method of claim 1 wherein the objects comprise small gas bubbles comprising gas of atomic number less than 40.

6. The method of claim 1 in which the objects comprise plastic beads.

7. The method of claim 6 in which the plastic beads have diameters less than 1 μm.

8. The method of claim 6, further comprising generating successive images of the objects at different period of time to detect a movement of the objects through the blood vessels.

9. The method of claim 1 in which the brighter fringes are caused by refracted rays overlapping other rays.

10. The method of claim 5, wherein irradiating the body includes irradiating the body to cause refraction of the penetrating radiation at boundaries of the small gas bubbles and generating edge enhancement features that include at least one of brighter or darker fringes,
  wherein adjusting the position of the body comprises moving the body from the first distance relative to the detector to the second distance relative to the detector, in which when the body is at the first distance relative to the detector, the at least one of brighter or darker fringes caused by refraction at the boundaries of the small gas bubbles are less visible, and when the body is at the second distance relative to the detector, the at least one of brighter or darker fringes caused by the refraction at the boundaries of the small gas bubbles are more visible, to cause the at least one of brighter or darker fringes produced by the refraction of the penetrating radiation occurring at boundaries of the small gas bubbles to be detected by the detector, and
  wherein generating an image comprises generating an image of the small gas bubbles based on detected radiation, the image including the at least one of brighter or darker fringes that indicate the boundaries of the small gas bubbles.

11. The method of claim 6, wherein irradiating the body includes irradiating the body to cause refraction of the penetrating radiation at boundaries of the plastic beads and generating edge enhancement features that include at least one of brighter or darker fringes,
  wherein adjusting the position of the body comprises moving the body from the first distance relative to the detector to the second distance relative to the detector, in which when the body is at the first distance relative to the detector, the at least one of brighter or darker fringes caused by refraction at the boundaries of the plastic beads are less visible, and when the body is at the second distance relative to the detector, the at least one of brighter or darker fringes caused by the refraction at the boundaries of the plastic beads are more visible, to cause the at least one of brighter or darker fringes produced by the refraction of the penetrating radiation occurring at the boundaries of the plastic beads to be detected by the detector, and
  wherein generating an image comprises generating an image of the plastic beads based on detected radiation, the image including the at least one of brighter or darker fringes that indicate the boundaries of the plastic beads.

12. An apparatus for angiography, comprising:
  a radiation source configured to irradiate blood vessels;
  a detector configured to detect the irradiated blood vessels;
  an imaging device configured to generate images of the blood vessels of a body with a refraction enhancement contrast agent introduced into the blood vessels based on penetrating radiation irradiated on the blood vessels,
  a stage configured to change a distance of the body with respect to the imaging device,
  the imaging device further configured to generate a first image with the blood vessels having a first distance with respect to the imaging device such that edge enhancements of the blood vessels based on refraction are significant, and
  the imaging device further configured to generate a second image of the blood vessels having a second distance, in which the second distance is different from the first distance, with respect to the imaging device such that the edge enhancements of the blood vessels based on refraction are not significant, the first image and the second image covering the same blood vessels; and
  an image acquisition system configured to generate a third image based on differences in the first image and the second image by subtracting the second image from the first image, wherein the third image has edge enhancement features indicating edges of the blood vessels, the edge enhancement features caused in part by refraction of the penetrating radiation at the edges of the blood vessels, and the edge enhancement features in the third image are more visible than the edge enhancement features in the first image.

13. The apparatus of claim 12, further comprising an injector for injecting the refraction enhancement contrast agent into the blood vessels.

14. A method comprising:
  irradiating blood vessels of a body with a penetrating radiation;
  placing the body on a stage in which the stage is positioned between a source of the penetrating radiation and a detector that detects the penetrating radiation;
  generating a first image of the blood vessels based on detected penetrating radiation, the first image having edge enhancement features that indicate edges of the blood vessels, in which the first image is generated with the blood vessels having a first distance with respect to an imaging device such that the edge enhancements of the blood vessels based on refraction are significant;
  generating a second image of the same blood vessels based on detected penetrating radiation, the second image having reduced edge enhancement features, in which the second image is generated with the blood vessels having a second distance via the stage with respect to the imaging device such that the edge enhancements of the blood vessels based on refraction are not significant; and
  generating a third image based on the differences between the first and second images by subtracting the second image from the first image, the third image having edge enhancement features with a contrast greater than the edge enhancement features of the first image.

15. The method of claim 14 wherein the edge enhancement features comprise a dark line adjacent to an edge of the blood vessel.

* * * * *